United States Patent [19]
Tindall et al.

[11] Patent Number: 5,516,639
[45] Date of Patent: May 14, 1996

[54] ANTIBODIES SPECIFIC FOR HUMAN PROSTATE GLANDULAR KALLKREIN

[75] Inventors: Donald J. Tindall; Charles Y. F. Young; George G. Klee, all of Rochester, Minn.

[73] Assignee: Mayo Foundation for Medical Education and Research, Rochester, Minn.

[21] Appl. No.: 96,946

[22] Filed: Jul. 22, 1993

[51] Int. Cl.⁶ .................................................. G01N 33/573
[52] U.S. Cl. .................... 435/7.4; 435/7.92; 435/7.93; 435/7.94; 435/240.26; 435/240.27; 436/64; 436/547; 436/548; 436/813; 530/326; 530/387.1; 530/388.1; 530/388.26
[58] Field of Search ..................... 435/7.4, 7.92, 435/7.93, 7.94, 240.26, 240.27; 530/387.1, 388.26, 388.1, 326; 436/547, 64, 813, 548

[56] References Cited

U.S. PATENT DOCUMENTS

| | | |
|---|---|---|
| 3,817,837 | 6/1974 | Rubenstein et al. . |
| 3,842,067 | 10/1974 | Sarantakis . |
| 3,850,752 | 11/1974 | Schuurs et al. . |
| 3,862,925 | 1/1975 | Sarantakis et al. . |
| 3,901,654 | 8/1975 | Gross . |
| 3,935,074 | 1/1976 | Rubenstein et al. . |
| 3,972,859 | 8/1976 | Fujino et al. . |
| 3,984,533 | 10/1976 | Uzgiris . |
| 3,996,345 | 12/1976 | Ullman et al. . |
| 4,034,074 | 7/1977 | Miles . |
| 4,092,408 | 5/1978 | Litt .................... 436/531 |
| 4,098,876 | 7/1978 | Piasio et al. . |
| 4,105,602 | 8/1978 | Colescott et al. . |
| 4,353,982 | 10/1982 | Gomez et al. .......... 435/962 |
| 4,371,515 | 2/1983 | Chu et al. . |
| 4,446,122 | 5/1984 | Chu et al. . |
| 4,487,715 | 12/1984 | Nitecki et al. . |
| 4,629,783 | 12/1986 | Cosand . |
| 4,757,048 | 7/1988 | Lewickik et al. . |
| 4,792,528 | 12/1988 | Canfield et al. ........ 436/515 |

FOREIGN PATENT DOCUMENTS 0297913  1/1989  European Pat. Off. .

OTHER PUBLICATIONS

Tijssen, P. Practice and Theory of Enzyme Immunoassays. Laboratory Techniques in Biochemistry and Molecular Biology vol. 15 (R. H. Burdon, ed.) New York: Elsevier, 1985, pp. 43–78 95–121, 297–384.

A. Lundwall, "Characterization of the gene for Prostate-specific antigen, a human glandular kallikrein", *Biochem. Biophys. Research Comm.*, 161, 1151–1159 (Jun. 30, 1989).

L. J. Schedlich et al., "Kallikrein genes: cloning in man and expression in rat renal hypertension", *Journal of Hypertension Supplement*, vol. 6, Supp. 4, S395–S398 (Dec. 1988).

C. Y.–F. Young et al., "Hormonal Regulation of Prostate-specific Antigen Messenger RNA in Human Prostatic Adenocarcinoma Cell Line LNCaP", *Cancer Research*, 51, 3748–3752 (Jul. 15, 1991).

P. Andrews et al., "Tumor–promoting Phorbol Ester Down-Regulates the Androgen Induction of Prostate-specific Antigen in a Human Prostatic Adenocarcinoma Cell Line", *Cancer Research*, 52, 1525–1529 (1992).

A. Baker et al., "Human Kidney Kallikrein: cDNA Cloning and Sequence Analysis", *DNA*, 4, 445 (1985).Berg et al., "A Common Nomenclature for Members of the Tissue (Glandular) Kallikrein Gene Families", *Recent Progress on Kinins*, Birkhauser Verlag Basel publisher, pp. 19–25 (1992).

(List continued on next page.)

Primary Examiner—Christine M. Nucker
Assistant Examiner—Jeffrey Stucker
Attorney, Agent, or Firm—Schwegman, Lundberg, Woessner & Kluth

[57] ABSTRACT

The present invention provides an isolated preparation of monoclonal or polyclonal antibodies which react specifically with human prostate-specific glandular kallikrein (hK2), but which do not cross-react with human prostate-specific antigen (PSA), as well as immunogenic hK2 antigens useful to provide such antibodies.

13 Claims, 4 Drawing Sheets

```
                                       41
hK2:  IVGGWECEKHSQPWQVAVWSHGWAHCGGVLVHPQWVLTAAHCLKKNSQVWLGRHN
hK3:  IVGGWECEKHSQPWQVLVASRGRAVCGGVLVHPQWVLTAAHCIRNKSVILLGRHS

56
      LFEPEDTGQRVPVSHSFPHPLYNMSLLKHQSLRPDEDSSHDLMLLRLSEPAKIT
      LFHPEDTGQVFQVSTSFPHPLYDMSLLKNRFLRPGDDSSHDLMLLRLSEPAELT 110                                              153
      DVVKVLGLPTQEPALGTTCYASGWGSIEPEEFLRPRSLQCVSLHLLSNDMCA
      DAVKVMDLPTQEPALGTTCYASGWGSIEPEEFLTPKKLQCVQLHVISNDVCA 162    167
      RAYSEKVTEFMLCAGLWTGGKDTCGGDSGGPLVCNGVLQGITSWGPEPCALPEKP
      QVHPQKVTKFMLCAGRWTGGKSTCSGDSGGPLVCNGVLQGITSWGSEPCALPERP 217                    237
      AVYTKVVHYRKWIKDTIAANP
      SLYTKVVHYRKWIKDTIVANP
```

OTHER PUBLICATIONS

Carpino et al., "The 9–Fluorenylmethoxycarbonyl Amino-–Protecting Group", *J. Org. Chem.*, 37, 3404 (1972).

Chang et al., "Solid–Phase Peptide Synthesis Using Mild Base Cleavage of $N^{alpha}$–Fluorenylmethyloxycarbonylamino Acids, Exemplified by a Synthesis of Dihydrosomatostatin", *Int. J. Pept. Pro. Res.*, 11, 246 (1978).

P. Chapdelaine, "High Level of Expression in the Prostate of a Human Glandular Kallikrein mRNA Related to Prostate–Specific Antigen", *FEBS Lett.*, 236:205 (1988).

J. Clements, "The Glandular Kallikrein Family of Enzymes: Tissue–Specific Expression and Hormonal Regulation", *Endocr. Rev.*, 10, 393 (1989).

M. Digby et al., "Human Prostate Specific Antigen (PSA) Gene: Structure and Linkage to the Kallikrein–like Gene", *Nuc. Acids Res.*, 17, 2137 (1989).

B. Evans et al., "Structure and Chromosomal Localization of the Human Renal Kallikrein Gene", *Biochemistry*, 27, 3124 (1988).

D. Fukusima et al., "Nucleotide Sequence of Cloned cDNA for Human Pancreatic Kallikrein", *Biochemistry*, 24, 8037 (1985).

P. Henttu et al., "Expression of the Gene Coding for Human Prostate–Specific Antigen and Related hGK–1 in Benign and Malignant Tumors of the Human Prostate", *Int. J. Cancer*, 45, 654–660 (1990).

M. LeBeau et al., "Report of the Committee on the Genetic Constitution of Chromosomes 18 and 19", *Cytogenet. Cell Genet.*, 51, 338 (1989).

F. Lottspeich et al., "N–Terminal Amino Acid Sequence of Human Urinary Kallikrein Homology with Other Serine Proteases", *Hoppe–Scyler's Z. Physiol. Chem.*, 360, 1947 (1979).

H. Lu et al., "Human Urinary Kallkrein", *Int. J. Peptide Protein Res.*, 33:237 (1989).

A. Lundwal et al., "Molecular Cloning of Human Prostate Specific Antigen cDNA", *FEBS Lett.*, 214, 317 (1987).

Merrifield, "Solid Phase Peptide Synthesis. I: The Synthesis of a Tetrapeptide", *J. Am. Chem. Soc.*, 85, 2149 (1963).

B. Montgomery et al., "Hormonal Regulation of Prostate–Specific Antigen (PSA) Glycoprotein in the Human Prostatic Adenocarcinoma Cell Line, LNCaP", *The Prostate*, 21, 63–73 (1992).

B. Morris, "hGK–1: A Kallikrein Gene Expressed in Human Prostate", *Clin. Exp. Pharmacol. Physiol.*, 16, 345–351 (1989).

P. Murtha et al., "Androgen Induction of a Human Prostate–Specific Kallikrein, hKLK2: Characterization of an Androgen Response Element in the 5' Promoter Region of the Gene", *Biochemistry*, 32:6459–6464 (1993).

G. Paradis et al., "Looking for Human Glandular Kallikrein–1 in the Prostate", *The Prostate*, 15, 343–353 (1989).

S. Qiu et al., "In Situ Hybridization of Prostate–Specific Antigen mRNA in Human Prostate", *J. Urology*, 144, 1550–1556 (1990).

P. Riegman et al., "Characterization of the Prostate–Specific Antigen Gene: A Novel Human Kallikrein–Like Gene", *Biochem. Biophys. Res. Comm.*, 159, 95 (1989).

P. Riegman et al., "The Prostate–Specific Antigen Gene and the Human Glandular Kallikrein–1 Gene are Tandemly Located on Chromosome 19", *FEBS Lett.*, 247, 123 (1989).

H. Ropers et al., "Report of the Committee on the Genetic Constitution of Chromosome 19", *Cytogenet. Cell Genet.*, 55, 218 (1990).

L. Schedlich et al., "Primary Structure of a Human Glandular Kallikrein Gene", *DNA* 6, 429–437 (1987).

L. Schedlich et al., "Three *Alu* Repeated Sequences Associated with a Human Glandular Kallikrein Gene", *Clin. Exper. Pharmacology & Physiology*, 15, 339–344 (1988).

P. Schulz et al., "Sequency of a cDNA Clone Encompassing the Complete Mature Human Prostate Specific Antigen (PSA) and an Unspliced Leader Sequence", *Nuc. Acids Res.*, 16, 6226 (1988).

G. Sutherland et al., "Human Prostate–Specific Antigen (APS) is a Member of the Glandular Kallikrein Gene Family at 19q13", *Cytogenet. Cell Genet.*, 48, 205 (1988).

K. Watt et al., "Human Prostate–Specific Antigen: Structural and Functional Similarity with Serine Proteases", *PNAS USA*, 83, 3166 (1986).

C. Young et al., "Tissue–Specific and Hormonal Regulation of Human Prostate–Specific Glandular Kallikrein", *Biochemistry* 31, 818–824 (1992).

Ransom, J. P. Practical Competitive Binding Assay Methods. St. Louis, MO: C.V. Mosby Co., 1976, pp.1–9, 54–61.

```
                     41
hK2 :  IVGGWECEKHSQPWQVAVWSHGWAHCGGVLVHPQWVLTAAHCLKKNSQVWLGRHN
hK3 :  IVGGWECEKHSQPWQVLVASRGRAVCGGVLVHPQWVLTAAHCIRNKSVILLGRHS

56
       LFEPEDTGQRVPVSHSFPHPLYNMSLLKHQSLRPDEDSSHDLMLLRLSEPAKIT
       LFHPEDTGQVFQVSTSFPHPLYDMSLLKNRFLRPGDDSSHDLMLLRLSEPAELT 110                                          153
       DVVKVLGLPTQEPALGTTCYASGWGSIEPEEFLRPRSLQCVSLHLLSNDMCA
       DAVKVMDLPTQEPALGTTCYASGWGSIEPEEFLTPKKLQCVQLHVISNDVCA 162   167
       RAYSEKVTEFMLCAGLWTGGKDTCGGDSGGPLVCNGVLQGITSWGPEPCALPEKP
       QVHPQKVTKFMLCAGRWTGGKSTCSGDSGGPLVCNGVLQGITSWGSEPCALPERP 217       237
       AVYTKVVHYRKWIKDTIAANP
       SLYTKVVHYRKWIKDTIVANP
```

ANTIBODIES SPECIFIC FOR HUMAN PROSTATE GLANDULAR KALLKREIN

The present invention was made with the support of the U.S. Government under Grant No. CA15093-19. The U.S. Government has certain rights in the invention.

BACKGROUND OF THE INVENTION

The glandular kallikreins are a subgroup of serine proteases which are involved in the post-translational processing of specific polypeptide precursors to their biologically active forms. The rodent kallikrein gene family consists of at least 25 genes. However, the human kallikrein gene family is much smaller, consisting of three members: prostate-specific antigen, human glandular kallikrein, and pancreatic/renal kallikrein. See J. A. Clements, *Endocr. Rev.*, 10, 393 (1989) and T. M. Chu et al. (U.S. Pat. No. 4,446,122). A common nomenclature for these members of the tissue (glandular) kallikrein gene families was recently adopted by T. Berg et al., in *Recent Progress on Kinins: Biochemistry and Molecular Biology of the Kallikrein-Dinin System. Aqents and Actions Supplements*, Vol. I, H. Fritz et al., eds., Birkhauser Verlag, Basel (1992), and is given on Table I, below.

homology of hK2 is greater with respect to hK3 and lower with respect to hK1; being 78% and 57%, respectively.

The similarities of gene structure and deduced amino acid sequences of these human kallikreins suggest that their evolution may involve the same ancestral gene. Moreover, as reported by Morris, cited supra.; P. Chapdelaine, *FEBS Lett.*, 236, 205 (1988); and Young, *Biochemistry*, 818, (1992), both hK2 and hK3 are expressed only in the human prostate, while expression of hK1 is limited to the pancreas, submandibular gland, kidney, and other nonprostate tissues. The putative sequence of a polypeptide reported to correspond to human urinary kallikrein was disclosed by Amgen (EPA 297,913).

Interestingly, the hK2 gene is located about 12 kbp downstream from the hK3 gene in a head-to-tail fashion on chromosome 19. See P. H. Riegman et al., *FEBS Lett.*, 247, 123 (1989). Thus, the relationship between hK2 and hK3 gene expression is very intriguing, especially with respect to their evolution and functional properties.

Tremendous interest has been generated in hK3 (PSA) because of the important role it plays as a marker to detect and to monitor the therapy of prostate carcinoma. Its usefulness as a marker is based on the elevated serum concentration of circulating hK3 proteins which are frequently

TABLE I

The Human Tissue Kallikrein Gene Family
(approved species designation: HSA)

| New Designation | Previous Designations | mRNA/cDNA | Protein | New Protein Designation |
|---|---|---|---|---|
| hKLK1 | KLK1[1,2] hRKALL[3] | λHK1[4] and phKK25[5] cDNAs | tissue kallikrein[6,14] (renal/pancreas/salivary) | hK1 |
| hKLK2 | KLK2[7], hGK-1[8], hGK-3[5] | | prostate-specific glandular kallikrein[15] | hK2 |
| hKLK3 | PSA[9], PA[10], APS[1,2] | λHPSA-1[11] and PSA[12] cDNAs | PSA[13] (prostate-specific antigen) | hK3 |

[1]G.R. Sutherland et al., Cytogenet. Cell Genet., 48, 205 (1988).
[2]M.M. LeBeau et al., Cytogenet. Cell Genet., 51, 338 (1989).
[3]B.A. Evans et al., Biochemistry, 27, 3124 (1988).
[4]A.R. Baker et al., DNA, 4, 445 (1985).
[5]D. Fukusima et al., Biochemistry, 24, 8037 (1985).
[6]F. Lottsperch et al., Hoppe-Scyler's Z. Physiol. Chem., 360, 1947 (1979).
[7]H.H. Ropers et al., Cytogenet. Cell Genet., 55, 218 (1990).
[8]L.J. Schedlich et al., DNA, 6, 429 (1987).
[9]M. Digby et al., Nuc. Acids Res., 17, 2137 (1989).
[10]P.H.J. Riegman et al., Biochem. Biophys. Res. Comm., 159, 95 (1989).
[11]A. Lundwal et al., FEBS Lett., 214, 317 (1987).
[12]P. Schulz et al., Nuc. Acids Res., 16, 6226 (1988).
[13]K.W.K. Watt et al., PNAS USA, 83, 3166 (1986).
[14]H.S. Lu et al., Int. J. Peptide Protein Res., 33, 237 (1989).
[15]C.Y.F. Young et al., Biochemistry, 818, (1992).

Amino acid sequences deduced by L. J. Schedlich et al., *DNA*, 6, 429 (1987) and B. J. Morris, *Clin. Exp. Pharmacol. Physiolo.*, 16, 345 (1989) indicate that hK2 may be a trypsin-like serine protease, whereas hK3 (PSA) is a chymotrypsin-like serine protease. Therefore, these two peptides may have different physiological functions.

Although the cDNA and genomic sequences for hK2 have been described, the functional hK2 protein has not yet been isolated and characterized from prostate tissues. The DNA sequence homology between hKLK2 and hKLK3 (exon regions) is 80%, whereas the homology between hKLK2 and hKLK1 is 65%. The deduced amino acid sequence associated with prostatic cancer. The serum concentration of hK3 has been found to be proportional to the cancer mass in untreated patients, but is also proportional to the volume of hyperplastic tissue in patients with benign prostatic hyperplasia (BPH). The serum levels of hK3 become reduced following prostate cancer therapy.

Currently, the Mayo Laboratory assays over 60,000 specimens for hK3 levels annually. Therefore, the high degree of sequence homology of hK2 with hK3 suggests that the levels both proteins may be useful in the diagnosis of prostate cancer. For example, the antibodies developed against hK3 now used in these assays could theoretically also recognize hK2, because of mutual contamination in the antigenic preparations used to develop the anti-hK3 antibodies, or because the above-mentioned structural similarities of the two proteins would yield cross-reacting antibodies. If elevated serum hK2 levels are not indicative of prostate cancer, then detection of hK2 by anti-hK3 antibodies could be responsible for the substantial percentage of false positive results which are observed in current hK3 assays. On the other hand, if circulating hK2 levels are also elevated above baseline levels in prostate cancer patients, detection of hK2 by hK2-specific antibodies would provide an alternative, confirmatory assay for prostate cancer.

However, despite the information which can be ascertained about hK2 from the DNA sequence and the cDNA probes, very little is known about the hK2 protein itself. The reason for this is that the protein has not been purified and characterized, and no method exists for measuring the protein in either prostate plasma, seminal plasma or in blood serum.

Therefore, a need exists for antibodies to hK2 (hGK-1) which do not cross-react with hK3 (PSA). A further need exists for an assay to determine the presence and/or level of hK2 in a physiological sample, without detecting hK3, or conversely, for an assay that can detect the presence and/or level of hK3 in a sample which is unaffected by the presence of hK2 in the same sample. A further need exists for improved and/or alternative methods to detect, stage and follow the course of prostate cancer.

BRIEF DESCRIPTION OF THE INVENTION

The present invention provides a purified antibody which binds to (or "reacts with") an epitope on human prostate-specific glandular kallikrein (hK2) but which does not significantly bind to prostate-specific antigen (hK3). The antibody of the present invention will thus bind specifically to purified preparations of hK2, to hK2 present in prostate plasma, seminal plasma, blood serum and other physiological fluids, as well as to subunits of the hK2 comprising an amino acid sequence including said epitope. Thus, the present invention also provides an isolated preparation of polyclonal antibodies comprising such a purified antibody, i.e., as can be prepared by immunizing a mammal with a purified antigenic subunit of hK2, so long as the polyclonal antibody preparation does not significantly cross-react with hK3. The antibody of the present invention can also be an isolated antibody preparation consisting essentially of a homogeneous population of anti-hK2 monoclonal antibodies, which can be prepared using conventional hybridoma methodology.

The present invention is based on our discovery that there is at least one peptide subunit of the hK2 protein which can be used to generate an antibody response in mammals, which antibodies do not significantly cross-react with hK3. This discovery was surprising in view of the high degree (78%) of sequence homology between hK2 and hK3, and the lack of any data in the prior art relating to the antigenicity of hK2. Thus, the present invention is also directed to a peptide of the formula (I):

His—Cys—Leu—Lys—Lys—Asn—Ser—Gln—Val—Trp—Leu—
Gly—Arg— His—Asn—Leu         (SEQ ID NO:1)

The peptide of formula I formally represents residues 41–56 of the deduced amino acid sequence of hK2, as said sequence was reported by L. J. Schedlish et al., *DNA*, 6, 429 (1987). Immunogenic or immunoreactive subunits of this peptide, preferably of at least 5 peptidyl units, which can also be specifically bound by specific anti-hK2 antibodies are also within the scope of the invention. Of course, the 41–56 sequence (SEQ ID NO:1) can comprise additional or alternative peptidyl residues that do not destroy its ability to cause an antigenic response that is specific to hK2, as discussed hereinbelow.

Figure 1:
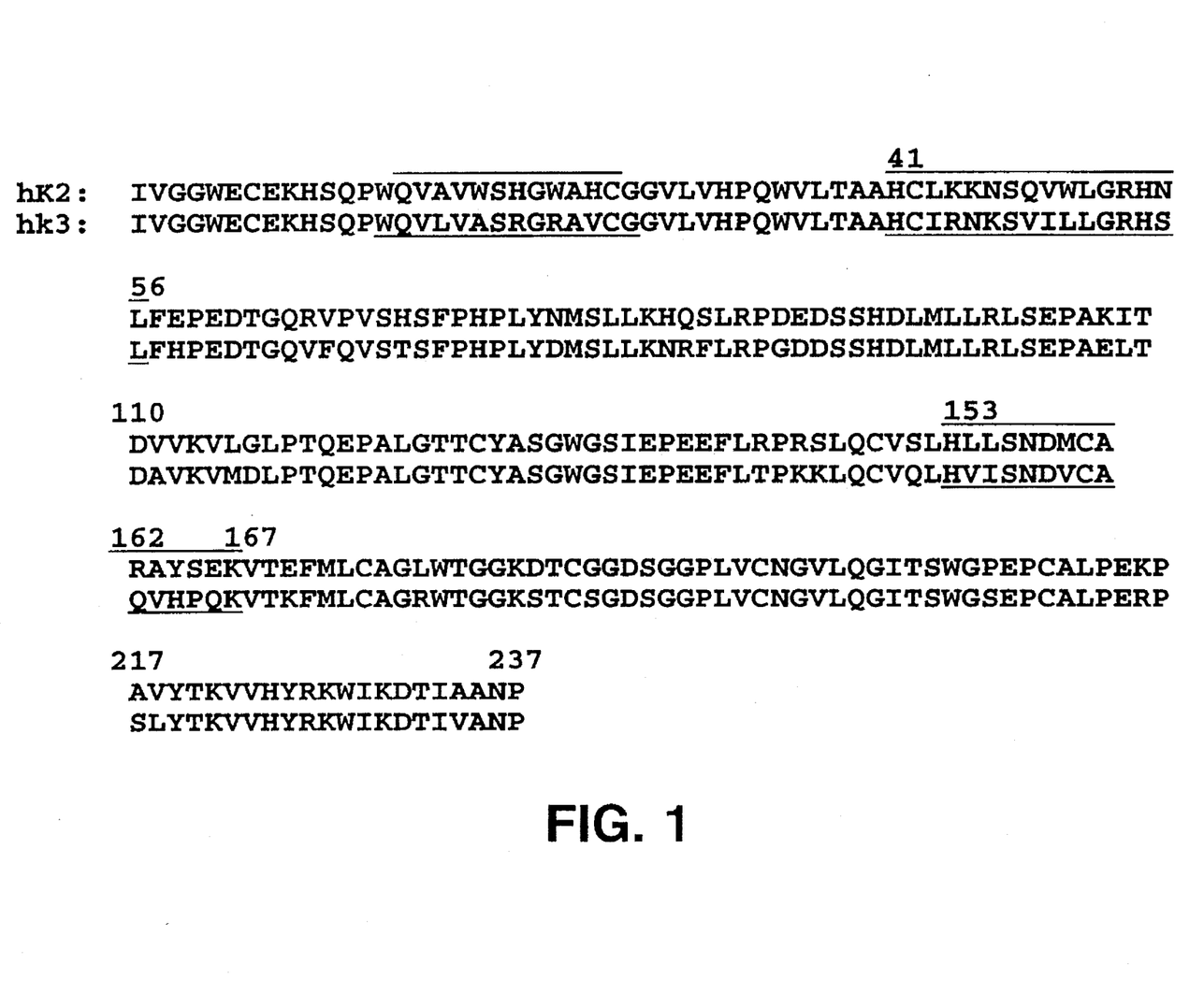
FIG. 1 depicts the amino acid sequences of hK2 (deduced from cDNA sequence) (SEQ ID NO:10) and hK3 (PSA) (SEQ ID NO:11). Underlined sequences denote nonhomologous regions used for development of monoclonal antibodies and polyclonal antibodies.

Furthermore, it is believed that other immunogenic hK2 subunits will also generate an antibody response that is unique to hK2, including hK2 (80–95) (SEQ ID NO:2), hK2 (104–119) (SEQ ID NO:3), hK2 (140–157) (SEQ ID NO:4), and hK2 (168–174) (SEQ ID NO:5), hK2 (8–26) (SEQ ID NO:6), hK2 (15–26) (SEQ ID N0:7), hK2 (153–167) (SEQ ID NO:8), and hK2 (210–235) (SEQ ID NO:9), wherein the numbers in parentheses identify the hK2 amino acid residues of the hK2 sequence disclosed in FIG. 1 and by Schedlish et al., cited above. Thus, these subunits, as well as monoclonal antibodies and polyclonal antibodies specific thereto, are also within the scope of the invention.

The present preparations of anti-hK2 antibodies can be immobilized, by adsorption or chemical binding to the surface of the solid substrate, such as a paper strip or a particulate solid, and used in a variety of immunological assays for hK2. In a simple embodiment, an immobilized preparation of hK2 antibodies is contacted with a sample, such as a liquid sample of a physiological fluid suspected of containing hK2, so that hK2 reacts with said anti-hK2 antibodies to form a binary complex. The presence of the binary complex is then detected, for example, by reacting the complex with a second antibody against a different antigenic site on the hK2 molecule to form a ternary complex. The second antibody comprises a detectable label such as a radiolabel, a fluorescent label, a chemiluminescent label or an enzyme or a binding site for a detectable label, since as one of the members of the avidin-biotin couple. Detection of the bound second antibody provides a measure of the amount of bound hK2.

Alternatively, the amount of hK2 in a sample can be detected, using a competitive immunoassay, i.e., by adding a limited amount of anti-hK2 antibody and a known amount of hK2 which itself comprises a detectable label or a binding site for a detectable label, precipitating the complex, and measuring the amount of free, labelled hK2, the amount of which is inversely proportional to the amount of hK2 in the sample. Many other immunoassays of related formats are available to the art, as described in, for example, Ortho Pharmaceutical Corp. (PCT/US87/00577); IAF (EPA 32649); and U.S. Pat. Nos. 4,629,783; 4,371515; 4,487,715; 3,817,837; 3,850,752; 3,901,654; 3,935,074; 3,984,533; 3,996,345; 4,034,074; and 4,098,876.

Single letter and three-letter abbreviations for the amino acid residues are A, alanine (Ala); R, arginine (Arg); N, asparagine (Asn); D, aspartic acid (Asp); C, cysteine (Cys); Q, glutamine (Gln); E, glutamic acid (Glu); G, glycine (Gly); H, histidine (His); I, isoleucine (Ile); L, leucine (Leu); K, lysine (Lys); F, phenylalanine (Phe); M, methionine (Met); P, proline (Pro); S, serine (Ser); T, threonine (Thr); W, tryptophan (Trp), Y, tyrosine (Tyr); V, valine (Val). In a given amino acid sequence of a peptide, the amino terminus of the peptide is at the left-hand end of the peptide and the carboxyl terminus is at the right-hand end.

DETAILED DESCRIPTION OF THE INVENTION hK2 Peptide Synthesis

The polypeptide of formula I, antigenic analogs and subunits thereof, or other hK2 subunit polypeptides can be synthesized by the solid phase peptide synthesis (or Merrifield) method. This established and widely used method, including the experimental procedures, is described in the following references: Stewart et al., *Solid Phase peptide Synthesis*, W. H. Freeman Co., San Francisco (1969); Merrifield, *J. Am. Chem. Soc.*, 85, 2149 (1963); Meienhofer in *Hormonal Proteins and Peptides*, Vol. 2, C.H. Li, ed., (Academic Press, 1973), pp. 48–267; and Barany and Merrifield in "The Peptides," Vol. 2, E. Gross and F. Meinenhofer, eds., Academic Press (1980), pp. 3–285. The synthesis commences from the carboxy-terminal end of the peptide using an alpha-amino protected amino acid. Fluorenylmethyloxy-carbonyl (Fmoc) or t-butyloxycarbonyl (Boc) protective groups can be used for all amino groups even through other protective groups are suitable, and the first protected amino acids can be esterified to chloromethylated polystyrene resin supports. The polystyrene resin support is preferably a copolymer of styrene with about 0.5 to 2% divinyl benzene as a cross-linking agent which causes the polystyrene polymer to be insoluble in certain organic solvents. See Carpino et al., *J. Org. Chem.*, 37, 3404 (1972); Meinhofer, *Int. J. Pept. Pro. Res.*, 11, 246 (1978); and Merrifield, *J. Am. Chem. Soc.*, 85, 2149 (1963). These and other methods of peptide synthesis are also exemplified by U.S. Pat. Nos. 3,862,925; 3,842,067; 3,972,859; 4,105,602 and 4,757,048.

The immobilized peptide is then N-deprotected and other amino acids having protected amino groups are added in a stepwise manner to the immobilized peptide. At the end of the procedure, the final peptide is cleaved from the resin, and any remaining protecting groups are removed, by treatment under acidic conditions such as, for example, with a mixture of hydrobromic acid and trifluoroacetic acid or with hydrofluoric acid, or the cleavage from the resin may be effected under basic conditions, for example, with triethylamine, the protecting groups then being removed under acidic conditions.

The cleaved peptide is isolated and purified by means well known in the art such as, for example, lyophilization followed by either exclusion or partition chromatography on polysaccharide gel media such as Sephadex G-25, or countercurrent distribution. The composition of the final peptide may be confirmed by amino acid analysis after degradation of the peptide by standard means.

The synthesis may use manual techniques or be completely automated, employing, for example, an Applied BioSystems 431A Peptide Synthesizer (Foster City, Calif.) or a Biosearch SAM II automatic peptide synthesizer (Biosearch, Inc., San Rafael, Calif.), following the instructions provided in the instruction manual and reagents supplied by the manufacturer. Disulfide bonds between Cys residues can be introduced by mild oxidation of the linear peptide by KCN as taughtin U.S. Pat. No. 4,757,048 at column 20.

Salts of carboxyl groups of the peptide may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

Acid addition salts of the polypeptides may be prepared by contacting thepolypeptide with one or more equivalents of the desired inorganic or organic acid, such as, for example, hydrochloric acid.

Esters of carboxyl groups of the polypeptides may be prepared by any of the usual methods known in the art for converting a carboxylic acid or precursor to an ester. One preferred method for preparing esters of the present polypeptides, when using the Merrifield synthesis technique described above, is to cleave the completed polypeptide from the resin in the presence of the desired alcohol either under basic or acidic conditions, depending upon the resin. Thus, the C-terminal end of the peptide when freed from the resin is directly esterified without isolation of the free acid.

Amides of the polypeptides of the present invention may also be prepared by techniques well known in the art for converting a carboxylic acid group or precursor, to an amide. A preferred method for amide formation at the C-terminal carboxyl group is to cleave the polypeptide from a solid support with an appropriate amine, or to cleave in the presence of an alcohol, yielding an ester, followed by aminolysis with the desired amine.

N-acyl derivatives of an amino group of the present polypeptidesmay be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

In addition, these peptide sequences can be modified by substituting one or two conservative amino acid substitutions for the positions specified, including substitutions which utilize the D rather than L form. As these peptides can be synthesized using standard solidphase techniques, for example, it is not necessary to confine the conservative substitutions to amino acids encoded by genes.

The invention is also directed to modified forms of the polypeptides. One or more of the residues of this polypeptide can be altered, so long as activity is retained. Conservative amino acid substitutions are preferred-that is, for example, aspartic-glutamic as acidic amino acids; lysine/arginine/histidine as basic amino acids; leucine/isoleucine, methionine/valine as hydrophobic amino acids; serine/glycine/alanine/threonine as hydrophilic amino acids. However, as the peptides need not be prepared by recombinant methods or from the gene, the substitutions may include nonencoded amino acids such as the D- or beta-amino forms.

Assay Formats

As well as being useful as an antigen to produce the present anti-hK2 antibodies, the peptide of formula I (41–56) (SEQ ID NO:1)) and its antigenic derivatives and subunits can also be immobilized and used as "capture antigens," to bind and immobilize anti-hK2 antibodies from a sample to be assayed for anti-hK2 antibodies (or subsequently, for anti-PSA antibodies). The bivalent complex of peptide and anti-hK2 antibody is then detected, e.g., in the case of a sample of human physiological material, by reacting it with an anti-human IgG antibody which comprises a detectable label or a binding site for a delectable label. In the latter case, the binding site is itself reacted with a compound specific for the binding site, which itself comprises a detectable label. Useful detectable labels include enzymes, radiolabels or fluorescent labels. The resultant ternary or quaternary complex is then detected and/or quantified via the detectable label, i.e., via an enzyme-substrate color-forming reaction, radioemission, agglomeration and the like.

Conversely, the anti-hK2 antibody of the present invention can be immobilized on the surface of a solid substrate and used as a capture antibody which can specifically bind to hK2 in a physiological fluid. Suitable substrates include particulate substrates such as polystyrene beads, the wells of plastic microtiter plates, paper or synthetic fiber test strips and the like. The immobilized antibody can then be contacted with the test sample to be assayed, e.g., with a physiological fluid such as semen, blood serum, prostate tissue homogenates, prostate fluid, and the like. The resultant antibody-hK2 binary complex can then be detected with an anti-hK2 antibody or with a known anti-PSA (anti-hK3) antibody (due to the cross-reactivity of anti-PSA antibodies with hK2) such as rabbit anti-PSA serum. The resultant ternary complex is then detected using a commercially available anti-IgG antibody, such as goat anti-rabbit IgG, which binds to the bound rabbit anti-PSA antibody, and itself comprises a detectable label (such as a radiolabel, an enzyme or an acridinium group) or a binding site for a detectable label (such as would form the avidin-biotin complex).

The anti-hK2 antibody of the present invention can itself be coupled chemically to a detectable label or a binding site for a detectable label. For example, the antibodies can be labelled radioisotopically (e.g., by $^{125}I$) or conjugated directly to a detector enzyme (e.g., alkaline phosphatase or horse radish peroxidase), or can be labelled indirectly with a binding site for a detectable label, e.g., via biotinylation. The biotinylated antibody can then be detected by its ability to bind to an avidin-linked enzyme. If the second antibody is biotinylated, a detector enzyme conjugated to avidin will be subsequently added. The final step for detecting enzymes conjugated to monoclonal antibody or to avidin is the addition of a substrate appropriate for the enzyme to allow quantitative colorimetric detection of reaction product. The value (read in optical density units) can be converted to fmol of hK2 by reference to a standard curve generated in a control assay in which a standard extract of detergent-solubilized hK2 is added in graded concentrations to the immobilized anti-hK2 monoclonal antibody.

In an alternative assay format using this material, anti-PSA (hK3) antibody is used as the capture antibody and any hK2 bound from the test sample (with hK3) is detected by reaction of the binary complex with anti-hK2 antibody, which comprises a label or a binding site for a detectable label, to form a ternary complex.

Alternatively, the peptide of formula I can be labelled with a detectable label such as via one or more radiolabelled peptidyl residues which can be used to compete with endogenous hK2 for binding to anti-hK2 antibodies, i.e., as a "capture antigen" to bind to anti-hK2 antibodies in a sample of a physiological fluid, via various competitive immunoassay formats. For example, a competitive immunoassay format for hK-2 which uses the present immobilized anti-hK2 antibodies is carried out by:

(a) providing an amount of anti-hK2 antibodies attached to a solid surface;

(b) mixing the sample of physiological fluid to be tested with a known amount of polypeptide of formula (I) which comprises a detectable label, to produce a mixed sample;

(c) contacting said antibodies on said solid surface with said mixed sample for a sufficient time to allow immunological reactions to occur between said antibodies and said hK2, and between said antibodies and said labelled polypeptide;

(d) separating the solid surface from the mixed sample;

(e) detecting or determining the presence or amount of labelled polypeptide either bound to the antibodies on the solid surface or remaining in the mixed sample; and (f) determining from the result in step e) the presence or amount of said hK2 in said sample.

In another format which can detect endogenous hK2 in a sample by a competitive inhibition immunoassay, a known amount of anti-hK2 antibody is added to a sample containing an unknown amount of endogenous hK2. The known amount is selected to be less than the amount required to complex all of the hK2 suspected to be present, e.g., that would be present in a sample of the same amount of physiological fluid obtained from a patient known to be prostate cancer. Next, a known amount of the polypeptide of formula I or a subunit thereof, comprising a detectable label is added. If endogenous hK2 is present in the sample, fewer antibodies will be available to bind the labelled polypeptide, and it will remain free in solution. If no endogenous hK2 is present, the added labelled polypeptide will complex with the added anti-hK2 antibodies to form binary complexes. Next, the binary antibody-antigen complexes are precipitated by an anti-mammal IgG antibody (sheep, goat, mouse, etc.). The amount of radioactivity or other label in the precipitate (a ternary complex) is inversely proportional to the amount of endogenous hK2 that is present in the sample, e.g., a pellet containing reduced amounts of radioactivity is indicative of the presence of endogenous hK2.

The use of immunometric assays combining two or more anti-hK2 antisera should produce both increased detection limits and better specificity. When antisera to two unique parts of the hK2 molecule are used in a "sandwich" assay the crossreactivity of related compound is greatly diminished. If several antisera are used simultaneously to immune extract hK2 then greater affinity may be obtained due to possible synergistic cooperative interactions, as described by P. H. Ehrlich et al., *J. Immunol.*, 131, 1906 (1983). Furthermore, if specific immunoextraction antibodies are used that uniquely bind to hK2, then a signal antibody which binds to both hK2 and hK3 could be used to detect the resulting complex. An assay can also be developed which would measure both hK3 and hK2 using specific anti-hK2 and anti-hK3 capture antibodies on the same support and a common signal antibody. Conversely, if a common antibody is used for the capture process, simultaneous quantification of both hK3 and hK2 could be achieved using two different signal detection systems attached to the specific anti-hK3 and anti-hK2 antibodies.

The anti-hK2 antibodies of the invention and the hK2 subunit peptides can be used in many other assay formats, such as competitive immunoassays, bead agglomeration assays and sandwich-type immunoassays, such as ELISA, as would be recognized by one of skill in this art.

The hK2-specific antibodies of the invention are also useful to isolate hK2 itself in essentially pure form from prostate tissue or fluids, or following production of hK2 by recombinant expressor systems, e.g., by using affinity-purification techniques. Pure hK2 itself can then be labelled and used in a competitive immunoassay when added to a fluid containing native hK2 as discussed above. Thus, these assays can detect and quantify the level of hK2 in a physiological sample and can be used to determine to what extent the binding of commercially available anti-hK3 antibodies to hK2 interferes with the ability of the antibodies to bind to, and thereby accurately detect and quantify, hK3. Furthermore, the present anti-hK2 antibodies can be used to determine whether or not hK2 protein levels are a useful marker to detect or stage prostatic cancer.

Monoclonal Antibodies

Alternatively to the conventional techniques for preparing antibodies in laboratory and farm animals, monoclonal antibodies against hK2 can be prepared using known hybridoma cell culture techniques. In general, this method involves preparing an antibody-producing fused cell line, e.g., of primary spleen cells fused with a compatible continuous line of myeloma cells, and growing the fused cells either in mass culture or in an animal species from which the myeloma cell line used was derived or is compatible. Such antibodies offer many advantages in comparison to those produced by inoculation into animals, as they are highly specific and sensitive and relatively "pure" immuno-chemically. Immunologically active fragments of the present antibodies are also within the scope of the present invention, e.g., the f(ab) fragment, as are partially humanized monoclonal antibodies.

The present immobilized antibodies, labelled antibodies, as well as free and labelled hK2 subunit poly-peptides, are conveniently packaged in kit form, wherein two or more of the various immunoreagents will be separately packaged in preselected amounts, within the outer packaging of the kit, which may be a box, envelope, or the like. The packaging also preferably comprises instruction means, such as a printed insert, a label, a tag, a cassette tape and the like, instructing the user in the practice of the assay format.

For example, one such diagnostic kit for detecting or determining antibodies to hK2 comprises packaging containing, separately packaged: (a) a solid surface, such as a fibrous test strip, a multi-well microtiter plate, a test tube, or beads, having bound thereto the peptide of formula I; and (b) labelled anti-human immunoglobulin. A second embodiment of a diagnostic kit for detecting or determining hK2 comprises packaging containing, separately packaged: (a) a solid surface having bound thereto antibodies to the polypeptide of formula I; and (b) a known amount of (a) antibodies specific to hK2 or (b) antibodies to hK2 which also bind to hK3, wherein said antibodies comprise a detectable label, or a binding site for a detectable label. A third embodiment of a diagnostic kit for detecting hK can comprise, in packaged association, separately packaged amounts of: (a) an hK2-specific antibody; (b) the labelled polypeptide of formula I; and (c) an anti-mammalian immunoglobulin.

The invention will be further described by reference to the following detailed examples.

EXAMPLE 1

Development and Purification of Polyclonal Antisera and Monoclonal Antibodies

Starting from the published putative amino acid sequence of hK2, a series of amino acid sequences were identified as possible candidates to give rise to antibodies unique for hGK-1. (See FIG. 1.) Peptides corresponding to each of these sequences were synthesized by 9-fluorenyl methoxy carbonyl (FMOC) strategy and purified by reverse-phase HPLC. These peptides then were sequenced to confirm their structure.

Peptides (41–56 and 153–167) were conjugated to keyhole limpet hemocyanin (KLH). Sheep, mice or goats were immunized with 100 µg of conjugated peptide (peptides of 41–56 and 153–167 into one sheep each, s.c., peptides 8–26, 15–26, 43–66, 153–167 and 210–235 into one goat each, s.c., and peptides 8–26, 15–26, 41–56, 43–66, 153–167 and 210–235 into four mice each, s.c.) in complete Freunds adjuvant (CFA) and boosted at 3 week intervals with 100 µg peptide in incomplete Freunds adjuvant (IFA). Subsequently, 5 goats and 24 Balb/c mice were immunized with these peptides. A combination of KLH conjugated peptide (100 µg), plus free peptide (100 µg), were used for this second immunization program.

After the first three immunizations, the blood of the animals was tested for antibody 6 to 10 days following each immunization. Peptides were immobilized on 0.25 inch polystyrene beads (Clifton, Clifton Heights, Pa.) by incubating 1 µg of peptide (conjugated to bovine serum albumin (BSA)) per bead in pH 9.6 carbonate buffer over night at 4° C. The beads then were washed three times with 0.01M phosphate buffered saline (PBS), pH 7.4 with 0.1% tween 20 and blocked with 1% skim milk plus 1% BSA. These beads were incubated for 18 hr. at 4° C. with 250 µL of 1:100, 1:1000 and 1:10,000 dilutions of the animal sera. Following three washes, 250 µL of rabbit anti-sheep, anti-mouse or anti-goat antibody conjugated to horseradish peroxidase (Cappel-Organon Teknica Corporation, Durham, NC) was incubated with each bead for 3 hr. on a horizontal incubator at 150 rpm. The enzyme signal was quantified spectrophotometrically using ortho-phenylene-diamine as a substrate. Non-immune sera were used as a negative control and immune sera measurements were expressed as multiples of the control readings.

Lymphocytes from the spleens of mice with positive serum titers were fused with myeloma cells to produce hybridoma cells. Antibodies produced by clones of these cells were screened as described above. Positive clones were subcloned by limiting dilution and rescreened. Monoclonal hybridomas were injected into the peritoneal cavities of pristine primed mice to obtain ascitic fluid.

Both the polyclonal (sheep and goat) and the monoclonal antisera were purified before using them in immunoassays. Both types of antisera initially were subjected to an IgG separation by precipitation with saturated ammonium sulfate and size chromatography using an ultragel ACA-34 column. The polyclonal antisera was further affinity purified using columns produced by cyanogen-bromide coupling of the peptides to Sepharose 4B. The purified antibody was eluted from the columns with acidic PBS (pH 2.45).

Table II summarizes the data developed for antisera and for monoclonal antibodies which gave a signal of at least twice the preimmune level. The best initial antisera was produced in sheep with the hK2 (41–56) peptide. This antisera has been most extensively evaluated. A sample of this antisera has been deposited in The American Type Culture Collection, Rockville, Md. USA to fulfill Patent Office requirements and assigend ATCC Designation 97079. Upon the granting of any patent from this application, all restrictions on the availability of this material will be irrevocably removed. The deposit wil be maintained for a period of at least 30 years after the date of the deposit, and for a period of at least five years after the most recent request for a sample. Of the other antisera, those against hK2 (210–235) have the highest immunoreactivity.

TABLE II

Antisera Against hK2

| Peptide | Source | Clone or Number | Dilution | Ratio to PreIm. |
|---|---|---|---|---|
| 8–26 | Hybridoma | 40-11 | 1:1000 | 2.5 |
| 8–26 | Hybridoma | 40-16 | 1:1000 | 2.9 |
| 8–26 | Goat | #4 | 1:1000 | 4.6 |
| 15–26 | Hybridoma | 22-4 | 1:100 | 3.9 |
| 15–26 | Hybridoma | 57-4 | 1:1000 | 2.0 |
| 41–56 | Sheep | 1498 | 1:10,000* | 6.7 |
| 41–56 | Hybridoma | 64-1 | 1:1000 | 1.9 |
| 41–56 | Hybridoma | 15-6 | 1:10,000 | ≈2 |
| 41–56 | Hybridoma | 15-19 | 1:10,000 | ≈2 |
| 153–167 | Hybridoma | 65-10 | 1:1000 | 2.6 |
| 153–167 | Hybridoma | 65-18 | 1:1000 | 3.4 |
| 153–167 | Hybridoma | 65-25 | 1:1000 | 2.0 |
| 153–167 | Hybridoma | 69-21 | 1:1000 | 3.1 |
| 153–167 | Goat | #1 | 1:10,000 | 2.5 |
| 210–235 | Hybridoma | 56-1 | 1:1000 | 7.3 |
| 210–235 | Hybridoma | 56-2 | 1:1000 | 6.9 |
| 210–235 | Hybridoma | 49-22 | 1:1000 | 4.5 |
| 210–235 | Goat | #5 | 1:1000 | 4.1 |

*Affinity purified

Figure 2:
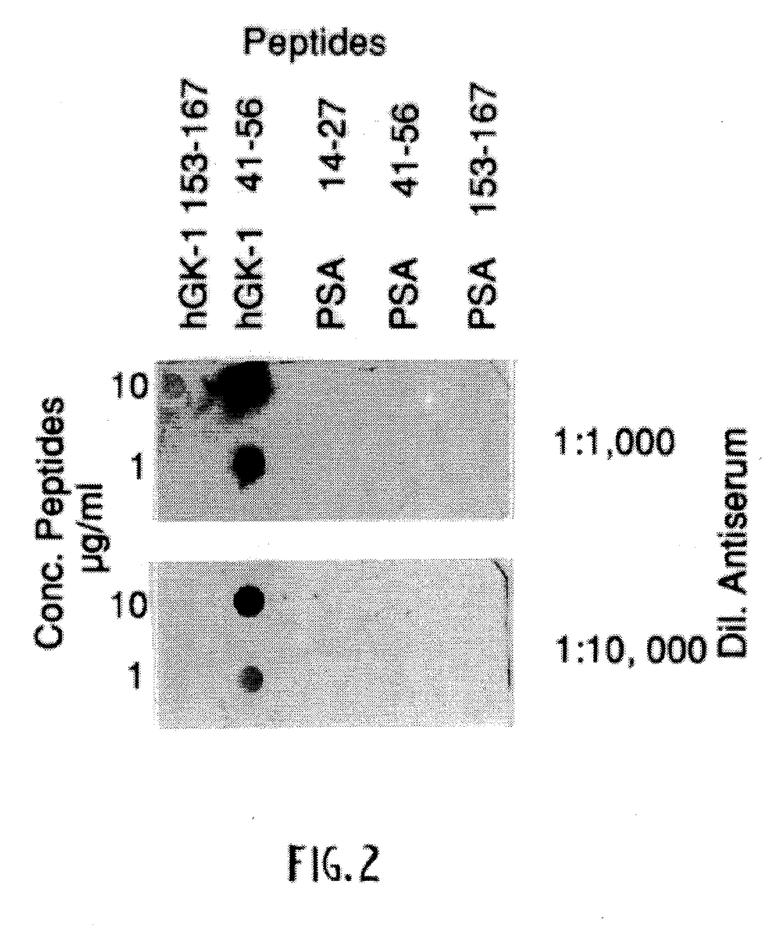
FIG. 2 depicts a dot-blot analysis of the hK2 (41–56) antiserum, comparing the binding thereto of hK2 (41–56), hK2 (153–167) and of hK3 (14–27), hK3 (41–56) and hK3 (153–167).

FIG. 2 shows a dot-blot analysis of anti-hK2 to hK2 and hK3 ("PSA") specific peptides. hK3 14–27 and hK3 41–56 and hK3 153–167 were derived from the hK3 polypeptide, and are homologous with similar areas of the hK2 protein. These peptides were dissolved in $H_2O$ and blotted onto nitrocellulose membranes at the concentrations indicated. An antiserum, obtained from sheep injected with the hK2 41–56 peptide conjugated with hemocyanin, was tested for its specificity and titer. The reaction of the primary antibody with the peptides on nitrocellulose membranes was detected by alkaline phosphatase conjugated with an anti-sheep IgG antibody. These data demonstrate that this anti-hK2 antisera has low cross-reactivity with hK3.

EXAMPLE 2

Competitive Immunoassays

Acridium N-hydroxysucinimide ester (London Diagnostics, Eden Prairie, Minn.) was attached to the amine group of the lysine residues of BSA-peptide conjugates. The coupling reaction was quenched using 20 g/L lysine monohydrochloride. The unreacted AE was removed by size exclusion chromatography using a Sephadex G-25 column followed by dialysis. The BSA-peptide conjugates were coupled with EDC (Pierce, Rockford, Ill.) using equal weights of EIA grade BSA and peptide.

A titer curve was first generated by incubating various dilutions of the purified sheep anti-hK2 (41–56) antibody with AE-labelled-BSA-peptide conjugate. The incubation period was 15 hours at 20° C. The bound antibody-label complexes were precipitated with donkey anti-sheep antisera and the signal in the isolated precipitate was quantitated using chemiluminescence.

Figure 3:
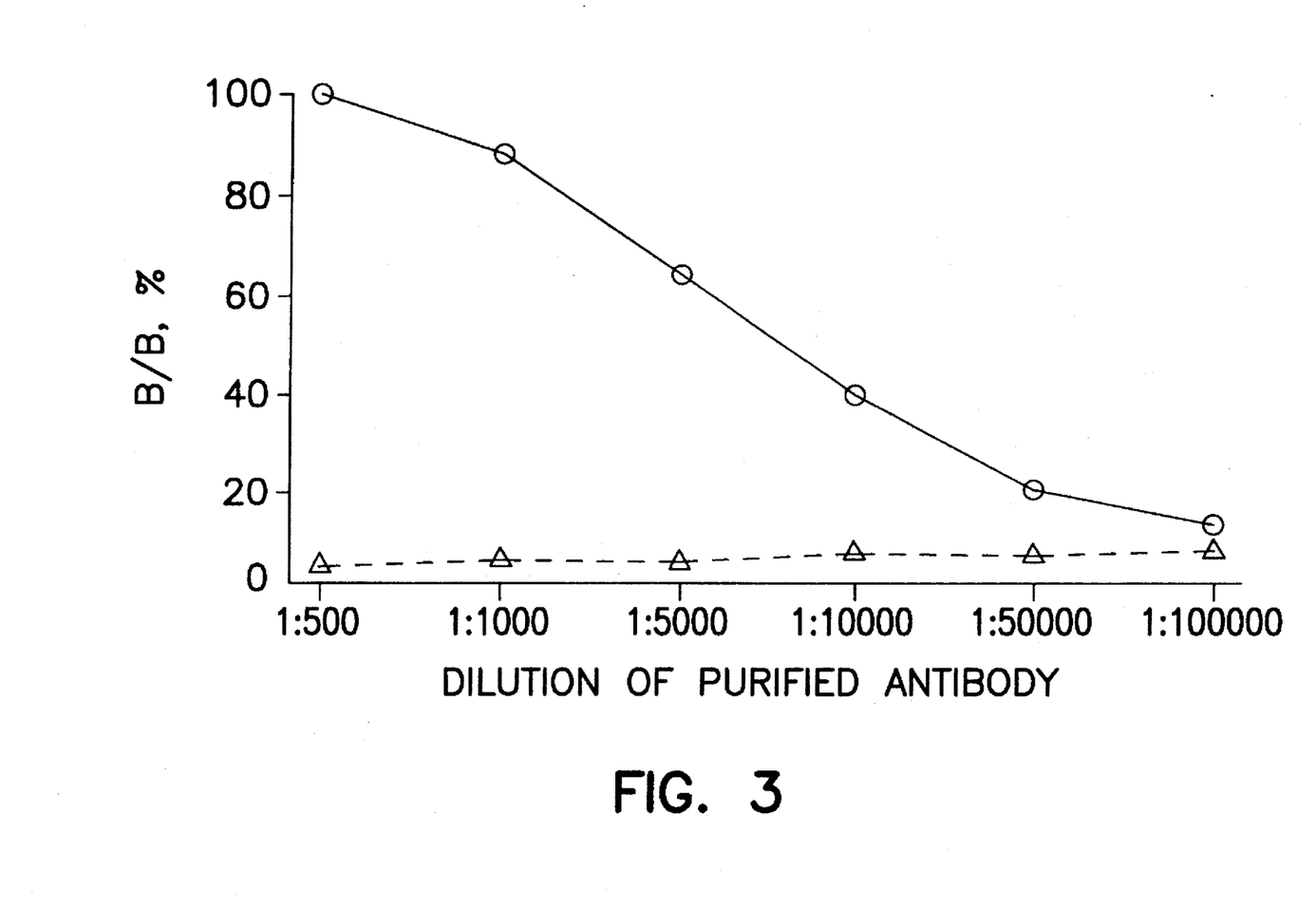
FIG. 3 depicts a titer curve showing binding of sheep anti-hK2 (41–56) antiserum to AE-labelled hK2 (41– 56)-BSA conjugate (o) compared to the binding of non-immune sheep serum (Δ).

FIG. 3 shows the titer curve of the affinity purified sheep hGK-1 (41–56) antibody (o) using non-immune sheep sera as a control (Δ). At an antibody dilution of 1:7000, the binding of the AE-labelled peptide to the antibody is approximately half maximum.

Assays were then developed based on competitive binding of the sheep antisera to the corresponding acridium-ester-(AE) labelled peptide versus unlabelled peptide. In addition to displacement by the unlabelled peptide, competition curves were established for the displacement of the hK2 (41–56) AE-peptide-BSA conjugate from a fixed amount of sheep anti-hK2 (41–56) by both prostate specific antigen (hK3) and hK2-type material immunoextracted from seminal fluid. Complexes which form after combining antibody with labelled hK2 (41–56) and the competing antigen, are precipitated, and the amount of label in the precipitate decreases as the ability of the test antigen to displace labelled hK2 (41–56) increases. The seminal fluid extract was obtained using an immunoaffinity column made by coupling purified sheep anti-hK2 (41–56) to an Aminolink198 column (Pierce, Rockford, Ill.). The immunoreactive material was eluted from the column with 0.1M glycine pH 2.8 and neutralized with 1M Tris, pH 10.

Figure 4:
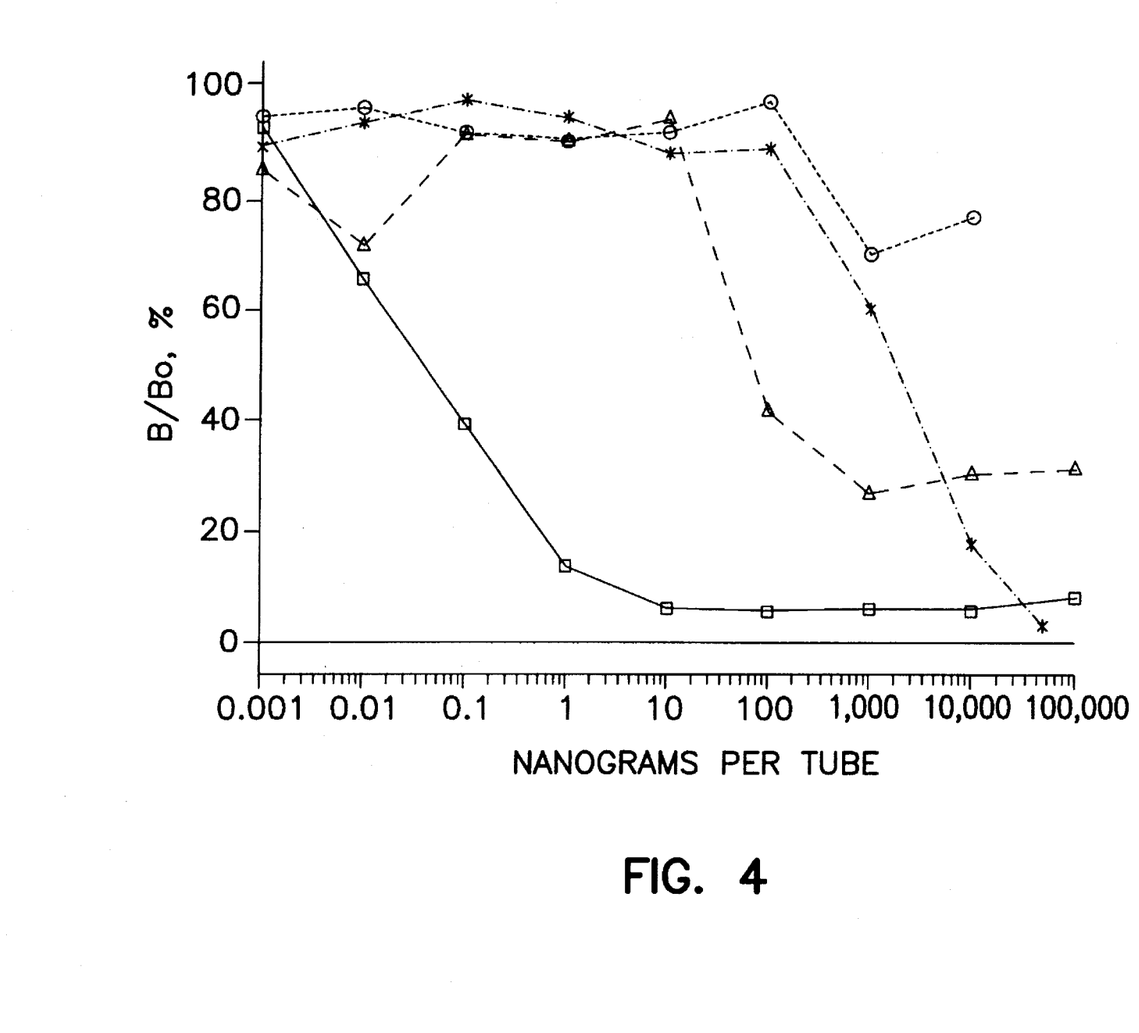
FIG. 4 depicts competitive displacement curves for sheep hK2 (41–56) antibody, wherein both hK2 (41–56) (□), hK3 peptide (41–56)(Δ) and a seminal fluid extract (*) can displace AE-labelled hK2 (41–56)-BSA conjugate from the antibody, while hK3 cannot significantly displace the conjugate (o).

The competitive displacement curve shown as (□) in FIG. 4 for hK2 (41–56) demonstrates that small amounts of this peptide can displace the label. Based on 20% displacement (80% B/Bo), the minimum detection limit of the competitive assay is approximately 0.03 ng/tube of hK2 (41–56). The cross-reactivity of the corresponding hK3 (41–56) peptide is less than 0.1% (Δ).

FIG. 4 also demonstrates that the material immunoextracted from seminal fluid (*) can displace the hK2 (41–56) label bound to the sheep anti-hK2 sera. This demonstrates that this material is immunoreactive. The open circles (o) show that the displacement with purified hK3 (Scripps Laboratories, San Diego, Calif.) is minimal. The immunoextracted material, even in the unpurified form, is more reactive than purified hK3 (Δ), but not as reactive as the hK2 peptide (□) on a weight basis. However, the hK2 peptide is composed of only 16 amino acids, whereas hK2 and hK3 are 237 amino acid polypeptides. Therefore, on a weight basis, one would expect the peptide to be about 15 times more reactive. The corresponding hK3 subunit polypeptide (41–56) could not substantially displace the AE-hK2 (41–56) label (Δ) (cross-reactivity ca. 1%), whereas hK2 (41–56) itself was also effective in displacing the hK2 (41–56) label (□). Therefore, the immunoreactive substance from seminal fluid is different from hK3, and probably is hK2.

These data demonstrate the utility of synthetic hK2 peptides based on putative sequences derived from hK2 cDNA in raising anti-hK2 peptide antibodies. The antibodies are specific against the hK2 peptides and do not recognize peptides from the homologous region in hK3. A peptide affinity column was used to purify an antibody which recognized a component in human seminal plasma, which was not hK3 (PSA). Therefore, the present invention provides an assay for hK2 in human seminal plasma which should be useful to assay for hK2 in human blood serum and in other fluids.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for detecting or determining hK2 in a sample of a human physiological fluid containing hK2 which comprises:

(a) providing, attached to a solid surface, an amount of purified antibodies which specifically react with human prostate specific glandular kallikrein (hK2), wherein said antibodies do not significantly react with prostate-specific serum antigen (hK3);

(b) contacting said antibodies on said solid surface with the sample to be tested for a sufficient time to allow the formation of binary complexes between at least a portion of said antibodies and a portion of said hK2; and (c) detecting or determining the presence or amount of hK2 complexed with said antibodies on said solid surface.

2. The method of claim 1 wherein, in step (c), the hK2 is reacted with an amount of antibodies which bind specifically to hK2 and do not bind to hK3, wherein said antibodies comprise a detectable label or bind to a detectable label, to form a detectable ternary complex.

3. A preparation of polyclonal antibodies having the reactivity with hK2 of ATCC 97079.

4. A purified antibody which specifically reacts with human prostate specific glandular kallikrein (hK2), wherein said antibody does not significantly react with prostate-specific serum antigen (hK3).

5. A purified antibody which specifically reacts with a polypeptide of the formula:

His—Cys—Leu—Lys—Lys—Asn—Ser—Gln—Val—Trp—Leu—Gly—Arg—His—Asn—Leu (SEQ ID NO:1)

or a subunit thereof, wherein said antibody does not significantly react with prostate specific antigen (hK3).

6. A preparation of polyclonal antibodies comprising the antibody of claims 1 or 5.

7. A preparation of monoclonal antibodies consisting essentially of the antibody of claims 1 or 5.

8. A solid phase having attached thereto the preparation of claim 6.

9. A solid phase having attached thereto the preparation of claim 7.

10. The solid phase of claim 8 which comprises a particulate matrix.

11. The solid phase of claim 9 which comprises a particulate matrix.

12. A competition method of detecting or determining hK2 in a sample of a human physiological fluid containing said hK2, comprising the steps of:
(a) providing an amount of the antibody of claim 5 attached to a solid surface, wherein said antibodies do not react with hK3;
(b) mixing the sample to be tested with a known amount of a polypeptide of the formula:

His—Cys—Leu—Lys—Lys—Asn—Ser—GLn—Val—Trp—Leu—Gly—Arg—His—Asn—Leu (SEQ ID NO: 1) or an immunoreactive subunit thereof, that binds to an antibody which specifically binds to hK2, wherein said antibody does not bind to hK3, which comprises a detectable label, to produce a mixed sample;
(c) contacting said antibodies on said solid surface with said mixed sample for a sufficient time to allow immunologic reactions to occur between said antibody and said hK2 and between said antibody and said labelled polypeptide;
(d) separating the solid surface from the mixed sample;
(e) detecting or determining the presence or amount of labelled polypeptide either bound to the antibody or the solid surface or remaining in the mixed sample; and
(f) determining from the result in step (e) the presence or amount of said hK2 in said sample.

13. A diagnostic kit for detecting or determining hK2 which comprises packaging, containing, separately packaged:
(a) a solid surface having bound thereto antibodies to a polypeptide of the formula:

His—Cys—Leu—Lys—Lys—Asn—Ser—Gln—Val—Trp—Leu—Gly—Arg—His—Asn—Leu (SEQ ID NO: 1) or an immunoreactive subunit thereof, that binds to an antibody which specifically binds to hK2, wherein said antibody does not bind to hK3; and
(b) a known amount of (a) the antibody of claims 4 or 5, wherein the antibody is detectably labelled or binds to a detectable label.

* * * * *

UNITED STATES PATENT AND TRADEMARK OFFICE
CERTIFICATE OF CORRECTION

PATENT NO. : 5,516,639
DATED : May 14, 1996
INVENTOR(S) : Donald J. Tindall, et. al.

It is certified that error appears in the above-indentified patent and that said Letters Patent is hereby corrected as shown below:

Title page, item [54] and col. 1, line 2, delete "KALLKREIN" and insert --KALLIKREIN--therefor.
Column 21, line 12, delete "specificaHy" and insert --specifically--.
Column 21, line 20, delete "claims 1 or 5" and isnert -- claims 4 or 5--.
Column 21, line 22, delete "claims 1 or 5" and insert --claims 4 or 5--.

Signed and Sealed this

Seventeenth Day of December, 1996

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear     ( i i ) MOLECULE TYPE: peptide     ( v i i ) IMMEDIATE SOURCE:
        ( B ) CLONE: Residues 41-56 of the deduced amino acid
            sequence of hK2

( x i ) SEQUENCE DESCRIPTION: SEQ ID NO:1:

```
His Cys Leu Lys Lys Asn Ser Gln Val Trp Leu Gly Arg His Asn Leu
 1               5                  10                  15
```

( 2 ) INFORMATION FOR SEQ ID NO:2:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear     ( i i ) MOLECULE TYPE: peptide     ( v i i ) IMMEDIATE SOURCE:
        ( B ) CLONE: hK2 amino acid residues 80-95

( x i ) SEQUENCE DESCRIPTION: SEQ ID NO:2:

```
Ser Leu Leu Lys His Gln Ser Leu Arg Pro Asp Glu Asp Ser Ser His
 1               5                  10                  15
```

( 2 ) INFORMATION FOR SEQ ID NO:3:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear     ( i i ) MOLECULE TYPE: peptide     ( v i i ) IMMEDIATE SOURCE:
        ( B ) CLONE: hK2 amino acid residues 104-119

( x i ) SEQUENCE DESCRIPTION: SEQ ID NO:3:

```
Glu Pro Ala Lys Ile Thr Asp Val Val Lys Val Leu Gly Leu Pro Thr
 1               5                  10                  15
```

( 2 ) INFORMATION FOR SEQ ID NO:4:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear     ( i i ) MOLECULE TYPE: peptide     ( v i i ) IMMEDIATE SOURCE:
        ( B ) CLONE: hK2 amino acid residues 140-157

( x i ) SEQUENCE DESCRIPTION: SEQ ID NO:4:

```
        Glu  Phe  Leu  Arg  Pro  Arg  Ser  Leu  Gln  Cys  Val  Ser  Leu  His  Leu  Leu
        1              5                        10                            15

Ser  Asn
```

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear     ( i i ) MOLECULE TYPE: peptide     ( v i i ) IMMEDIATE SOURCE:
        ( B ) CLONE: hK2 amino acid residues 168-174

( x i ) SEQUENCE DESCRIPTION: SEQ ID NO:5:

```
        Val  Thr  Glu  Phe  Met  Leu  Cys
        1                   5
```

( 2 ) INFORMATION FOR SEQ ID NO:6:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear     ( i i ) MOLECULE TYPE: peptide     ( v i i ) IMMEDIATE SOURCE:
        ( B ) CLONE: hK2 amino acid residues 8- 26

( x i ) SEQUENCE DESCRIPTION: SEQ ID NO:6:

```
        Glu  Lys  His  Ser  Gln  Pro  Trp  Gln  Val  Ala  Val  Trp  Ser  His  Gly  Trp
        1              5                        10                            15

Ala  His  Cys
```

( 2 ) INFORMATION FOR SEQ ID NO:7:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear     ( i i ) MOLECULE TYPE: peptide     ( v i i ) IMMEDIATE SOURCE:
        ( B ) CLONE: hK2 amino acid residues 15-26

( x i ) SEQUENCE DESCRIPTION: SEQ ID NO:7:

```
        Gln  Val  Ala  Val  Trp  Ser  His  Gly  Trp  Ala  His  Cys
        1                   5                        10
```

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear     ( i i ) MOLECULE TYPE: peptide     ( v i i ) IMMEDIATE SOURCE:
        ( B ) CLONE: hK2 amino acid residues 153-157

( x i ) SEQUENCE DESCRIPTION: SEQ ID NO:8:

5,516,639

(2) INFORMATION FOR SEQ ID NO:9:

(i) SEQUENCE CHARACTERISTICS:
    (A) LENGTH: 26 amino acids
    (B) TYPE: amino acid
    (C) STRANDEDNESS: single
    (D) TOPOLOGY: linear   (ii) MOLECULE TYPE: peptide   (vii) IMMEDIATE SOURCE:
    (B) CLONE: hK2 amino acid residues 210-235

(xi) SEQUENCE DESCRIPTION: SEQ ID NO:9:

```
His Leu Leu Ser Asn
 1               5
```

```
Cys Ala Leu Pro Glu Lys Pro Ala Val Tyr Thr Lys Val Val His Tyr
 1               5                  10                  15

Arg Lys Trp Ile Lys Asp Thr Ile Ala Ala
                20                  25
```

(2) INFORMATION FOR SEQ ID NO:10:

(i) SEQUENCE CHARACTERISTICS:
    (A) LENGTH: 237 amino acids
    (B) TYPE: amino acid
    (C) STRANDEDNESS: single
    (D) TOPOLOGY: linear   (ii) MOLECULE TYPE: peptide   (vii) IMMEDIATE SOURCE:
    (B) CLONE: Amino acid sequence of hK2
      (deduced from cDNA sequence)

(xi) SEQUENCE DESCRIPTION: SEQ ID NO:10:

```
Ile Val Gly Gly Trp Glu Cys Glu Lys His Ser Gln Pro Trp Gln Val
 1               5                  10                  15

Ala Val Trp Ser His Gly Trp Ala His Cys Gly Gly Val Leu Val His
                20                  25                  30

Pro Gln Trp Val Leu Thr Ala Ala His Cys Leu Lys Lys Asn Ser Gln
                35                  40                  45

Val Trp Leu Gly Arg His Asn Leu Phe Glu Pro Glu Asp Thr Gly Gln
        50                  55                  60

Arg Val Pro Val Ser His Ser Phe Pro His Pro Leu Tyr Asn Met Ser
65                  70                  75                  80

Leu Leu Lys His Gln Ser Leu Arg Pro Asp Glu Asp Ser Ser His Asp
                85                  90                  95

Leu Met Leu Leu Arg Leu Ser Glu Pro Ala Lys Ile Thr Asp Val Val
                100                 105                 110

Lys Val Leu Gly Leu Pro Thr Gln Glu Pro Ala Leu Gly Thr Thr Cys
                115                 120                 125

Tyr Ala Ser Gly Trp Gly Ser Ile Glu Pro Glu Glu Phe Leu Arg Pro
        130                 135                 140

Arg Ser Leu Gln Cys Val Ser Leu His Leu Leu Ser Asn Asp Met Cys
145                 150                 155                 160

Ala Arg Ala Tyr Ser Glu Lys Val Thr Glu Phe Met Leu Cys Ala Gly
                165                 170                 175

Leu Trp Thr Gly Gly Lys Asp Thr Cys Gly Gly Asp Ser Gly Gly Pro
                180                 185                 190

Leu Val Cys Asn Gly Val Leu Gln Gly Ile Thr Ser Trp Gly Pro Glu
```

|   |   |   | 195 |   |   |   | 200 |   |   |   | 205 |   |   |
|---|---|---|---|---|---|---|---|---|---|---|---|---|---|
| Pro | Cys 210 | Ala | Leu | Pro | Glu | Lys 215 | Pro | Ala | Val | Tyr | Thr 220 | Lys | Val | Val | His |
| Tyr 225 | Arg | Lys | Trp | Ile | Lys 230 | Asp | Thr | Ile | Ala | Ala 235 | Asn | Pro |

( 2 ) INFORMATION FOR SEQ ID NO:11:

( i ) SEQUENCE CHARACTERISTICS:
        ( A ) LENGTH: 237 amino acids
        ( B ) TYPE: amino acid
        ( C ) STRANDEDNESS: single
        ( D ) TOPOLOGY: linear     ( i i ) MOLECULE TYPE: peptide     ( v i ) ORIGINAL SOURCE:
        ( A ) ORGANISM: Amino acid sequence of PSA (hK3)

( x i ) SEQUENCE DESCRIPTION: SEQ ID NO:11:

| Ile 1 | Val | Gly | Gly | Trp 5 | Glu | Cys | Glu | Lys | His 10 | Ser | Gln | Pro | Trp | Gln 15 | Val |
|---|---|---|---|---|---|---|---|---|---|---|---|---|---|---|---|
| Leu | Val | Ala | Ser 20 | Arg | Gly | Arg | Ala | Val 25 | Cys | Gly | Gly | Val | Leu 30 | Val | His |
| Pro | Gln | Trp 35 | Val | Leu | Thr | Ala | Ala 40 | His | Cys | Ile | Arg | Asn 45 | Lys | Ser | Val |
| Ile | Leu 50 | Leu | Gly | Arg | His | Ser 55 | Leu | Phe | His | Pro | Glu 60 | Asp | Thr | Gly | Gln |
| Val 65 | Phe | Gln | Val | Ser | Thr 70 | Ser | Phe | Pro | His | Pro 75 | Leu | Tyr | Asp | Met | Ser 80 |
| Leu | Leu | Lys | Asn | Arg 85 | Phe | Leu | Arg | Pro | Gly 90 | Asp | Asp | Ser | Ser | His 95 | Asp |
| Leu | Met | Leu | Leu 100 | Arg | Leu | Ser | Glu | Pro 105 | Ala | Glu | Leu | Thr | Asp 110 | Ala | Val |
| Lys | Val | Met 115 | Asp | Leu | Pro | Thr | Gln 120 | Glu | Pro | Ala | Leu | Gly 125 | Thr | Thr | Cys |
| Tyr | Ala 130 | Ser | Gly | Trp | Gly | Ser 135 | Ile | Glu | Pro | Glu | Glu 140 | Phe | Leu | Thr | Pro |
| Lys 145 | Lys | Leu | Gln | Cys | Val 150 | Gln | Leu | His | Val | Ile 155 | Ser | Asn | Asp | Val | Cys 160 |
| Ala | Gln | Val | His | Pro 165 | Gln | Lys | Val | Thr | Lys 170 | Phe | Met | Leu | Cys | Ala 175 | Gly |
| Arg | Trp | Thr | Gly 180 | Gly | Lys | Ser | Thr | Cys 185 | Ser | Gly | Asp | Ser | Gly 190 | Gly | Pro |
| Leu | Val | Cys 195 | Asn | Gly | Val | Leu | Gln 200 | Gly | Ile | Thr | Ser | Trp 205 | Gly | Ser | Glu |
| Pro | Cys 210 | Ala | Leu | Pro | Glu | Arg 215 | Pro | Ser | Leu | Tyr | Thr 220 | Lys | Val | Val | His |
| Tyr 225 | Arg | Lys | Trp | Ile | Lys 230 | Asp | Thr | Ile | Val | Ala 235 | Asn | Pro |